United States Patent [19]

Van Wie et al.

[11] Patent Number: 4,939,087
[45] Date of Patent: Jul. 3, 1990

[54] METHOD FOR CONTINUOUS CENTRIFUGAL BIOPROCESSING

[75] Inventors: Bernard J. Van Wie, Pullman; Michael L. Elliott, Richland; Thomas M. Brouns, Pullman, all of Wash.

[73] Assignee: Washington State University Research Foundation, Inc., Wash.

[21] Appl. No.: 48,718

[22] Filed: May 12, 1987

[51] Int. Cl.⁵ ............................................. C12N 5/02
[52] U.S. Cl. ........................ 435/240.25; 435/240.46; 435/240.47; 435/243; 435/255; 435/256; 435/286; 435/312; 435/813
[58] Field of Search ...................... 435/240.25, 240.46, 435/240.47, 243, 251.1, 255, 256, 284, 286, 312, 813

[56] References Cited

U.S. PATENT DOCUMENTS

| | | |
|---|---|---|
| 3,347,454 | 10/1967 | Bellamy, Jr. et al. |
| 3,737,096 | 6/1973 | Jones et al. |
| 3,748,101 | 7/1973 | Jones et al. |
| 3,825,175 | 7/1974 | Sartory . |
| 3,862,715 | 1/1975 | Remenyik . |
| 3,955,755 | 5/1976 | Breillatt, Jr. et al. |
| 3,986,442 | 10/1976 | Khoja et al. |
| 4,010,894 | 3/1977 | Kellogg et al. |
| 4,056,224 | 11/1977 | Loloachi . |
| 4,113,173 | 9/1978 | Loloachi . |
| 4,127,231 | 11/1978 | Khoja et al. |
| 4,132,349 | 1/1979 | Khoja et al. |
| 4,146,172 | 3/1979 | Cullis et al. |
| 4,322,298 | 3/1982 | Persidsky ........................... 210/787 |
| 4,591,445 | 5/1986 | Spinell et al. ........................ 422/101 |
| 4,665,027 | 5/1987 | Dale et al. ........................... 435/813 |

FOREIGN PATENT DOCUMENTS

| | | |
|---|---|---|
| 2717344 | 11/1979 | Fed. Rep. of Germany . |
| 2392725 | 12/1978 | France . |
| 2395785 | 1/1979 | France . |
| 7708858-1 | 7/1979 | Sweden . |

OTHER PUBLICATIONS

Abstract–Fourth Congress of the International Society for Artificial Organs, Nov. 14–17, 1983, Kopto Japan, Van Wie.
National Technical Information Service publication PB253569 "Flow-Through Centrifuge", Feb. 25, 1976.
Beckman Brochure–"Centrifugal Elutriation of Living Cells", D5534, 4SP66531-478-5B.

Primary Examiner—Robert J. Warden
Assistant Examiner—Timothy M. McMahon
Attorney, Agent, or Firm—Wells, St. John & Roberts

[57] ABSTRACT

Bioprocessing apparatus and method using centrifugal acceleration of cells to maintain a culture within a reaction zone. The reactor has an inflow at a relatively distance inlet and an outflow at an inwardly spaced point toward the rotational axis. The reaction chamber has an inwardly diverging zone with a velocity gradient which captures cells of varying sizes. A recycle system is preferably used to recycle medium containing nutrients for the culture microbes. Byproducts of the cells are removed by the circulated medium and can be extracted using a desired extraction process.

22 Claims, 9 Drawing Sheets

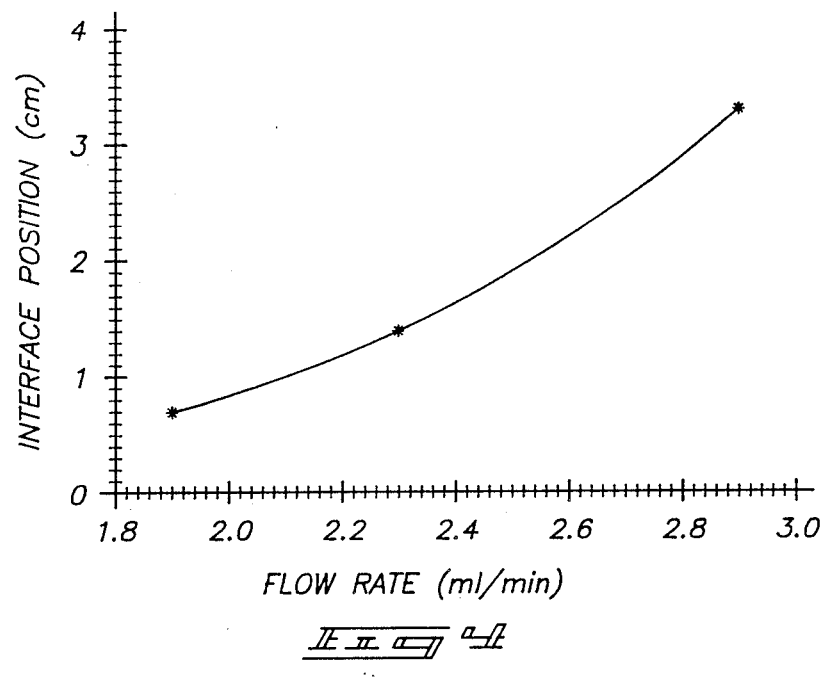
_FIG. 4_
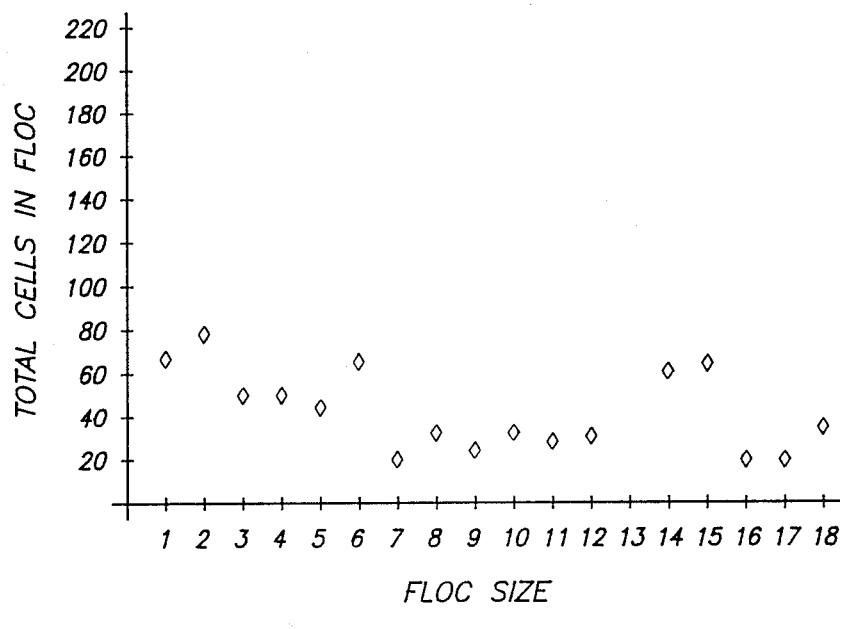
_FIG. 5_

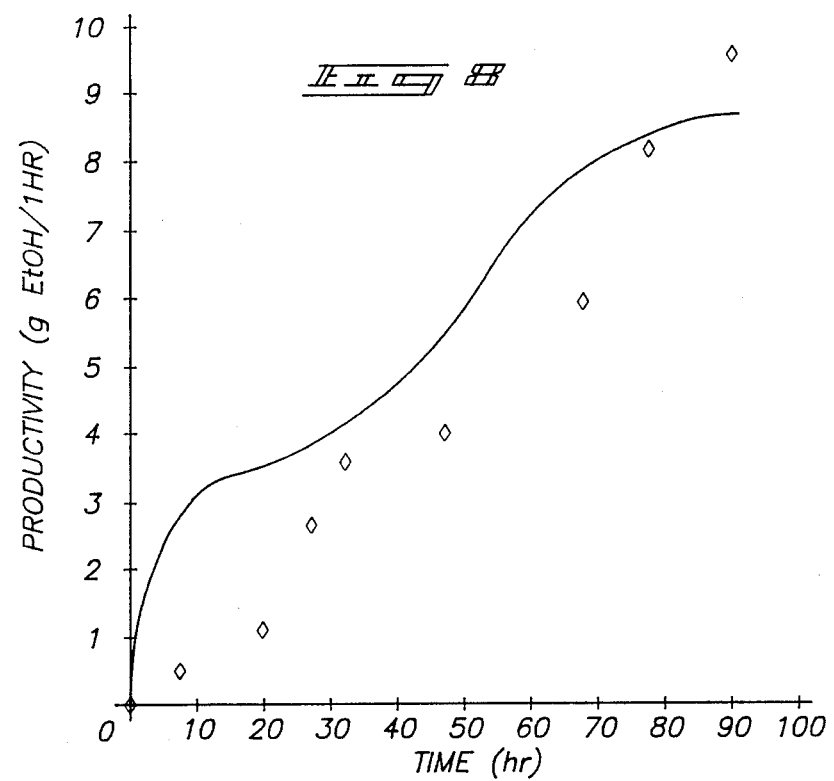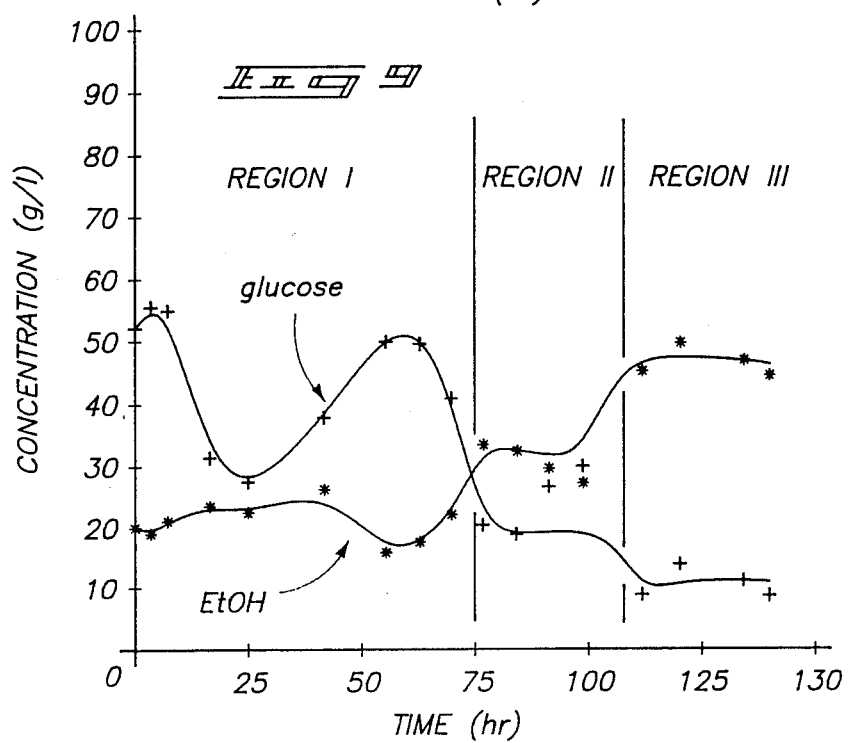

METHOD FOR CONTINUOUS CENTRIFUGAL BIOPROCESSING

TECHNICAL FIELD

The technical field of this invention is centrifugal culturing of microorganisms and cells and extraction of their byproducts.

BACKGROUND OF THE INVENTION

The current typical production processes for microorganisms and their byproducts involve culturing the microbes in flasks, vessels or tanks with suitable media in a batch type process. The cultures are then typically removed from the culture vessels and the desired cells or cell byproducts isolated using a variety of separation techniques. Typically the cell cultures are lost in the extraction process. Production of another batch requires substantial amounts of time for cell growth and population development prior to production of sufficient quantities of cell byproducts so as make the processes economic.

In some processes the desired cell product is maintained within the cell and accordingly cell lysis is necessary. In many other biological processes the desired products are excreted from the cells without the need for cell lysis. Continuous production techniques capable of culturing the cells and removing the desired products thus would provide greater production capability by eliminating the need to recreate a cell population in each batch.

Problems associated with the continuous extraction of cell products have been the desire to maintain high cell concentrations and provide gentle agitation of the cell suspensions to create good mass transfer to and from the cells for nutrition and product removal. These problems have not been fully solved using prior art techniques.

A further problem of prior art cell culturing procedures is the relative inability to accurately determine the defects of various production parameters on production rates. Production parameters such as reactor cell density, nutrient flow, agitation, possible inhibiting or enhancing affects due to high densities of cells or other parameters have been difficult to quantitatively determine using batch processing because of the numerous batches which must be produced and inherent variations in the populations and the resultant statistical variations attendant therewith. The addition of various cell culturing additives has also been hampered because of nonuniform concentrations in the culture due to reactions with cell products or metabolic reaction by the cells which may vary significantly from culture to culture.

In an attempt to procure kinetic information and improve productivities by providing higher cell concentrations many approaches have been developed, all with less than satisfactory results. For example, membrane filtration has been attempted, but it has two major drawbacks: large pressure drop which restricts substrate flow; and frequent clogging requiring cleaning or replacement of the membranes. Immobilization of cells in gels or on a solid supporting matrix such as a hollow fiber can be used to obtain high cell concentrations but these systems suffer from other disadvantages. One is that of limited heat and mass transfer to and from the cells. Another is the alteration of cell function through the process of immobilization on a solid support. With hollow fibers, damage to the integrity of fiber walls often occurs due to pressures exerted by the expanding cell mass. Fluidized bed tower reactors, although they eliminate the need for moving parts and have low capital costs, are limited to use with flocculating systems. Cell recycle also has been used but has a disadvantage in that cells are removed from the reactor for a period of time. This may cause cells to go into a stationary phase of growth which may take some time to reverse upon re-entrance to the fermentor. Several processes which use high cell densities combine reaction and liquid extraction of products in one unit. Shortcomings of these procedures are that the extraction solvent often has an inhibition effect on cell growth and multiplicaton. None of the above procedures offer a good technique to quantify the effects of cell crowding on intrinsic growth kinetics. It is felt that growth-limiting factors may regulate maximum cell concentrations, but presently these cell inhibition effects are not well understood.

In the development of kinetic models to describe cell mediated reaction processes, the rate of cell growth is important in order to describe both the rates of substrate utilization and of product formation. Since kinetic information concerning the very recent development of mammalian culture work is quite limited the following discussion will focus on yeast fermentation kinetics. It is expected that kinetic relationships for the animal cells in this research will taken on similar forms as those for fermentation. The intent of the current project will be to elaborate the most important parameters in determining mammalian cell growth rates.

In commercial fermentation processes it is the exponential cell growth rate, shown by the equation below, which is most important:

$$dX/dt = u\,X$$

where  $X$ = cell concentration
 $u$ = specific growth rate constant

The specific growth rate constant, u, in it's simplest form can be written as a function of the substrate concentration, S, and saturation constant, $K_s$, using the Monod equation:

$$u = u_o S/(K_s + S)$$

where $u_o$ = maximum specific cell growth rate Although the Monod equation is an over-simplification the model often adequately describes fermentation kinetics in low product or cell inhibition environments.

As product and cell concentrations are increased, concentrations are reached which causes inhibition effects. Product inhibition effects have been well characterized for many systems. However, until the recent emphasis on reactors with high cell concentrations, the inhibitory effects of cell crowding on intrinsic kinetics have not been of great importance. Inhibition may result from cell surface properties causing the transmission of growth inhibiting factors. A modified expression for the specific cell growth rate, which includes product and cell inhibition terms, appears below:

$$u = u_o(S/K_s + S))(1 - P/P_m)n(1 - X/X_m)m$$

-continued where  P = product concentration
       X = cell concentration
       $P_m$ = maximum product concentration at which cell growth ceases
       $X_m$ = maximum cell concentration at which cell growth ceases
       n = power factor indicating how strongly the product inhibition term affects specific cell growth rate
       m = power factor indicating how strongly the cell inhibition term affects specific cell growth rate Most models use a linear function to portray the relationship between specific growth rate and cell concentration. However, linear models have been shown to work well only at lower cell concentrations (5–10 g/l). At higher concentrations these are inaccurate and the exponential relationship for cell growth shown in equation (3), is more effective. An alternative form of the product inhibition term has been used by Aiba, et al. and Boulton, but it loses validity at higher product concentrations.

Substrate and product inhibition effects have been well studied for fermentation systems. However, the maximum cell concentration, $X_m$, and exponential power factor, m, in the cell inhibition term of equation (3) have yet to receive adequate attention. The lack of previous interest in the cell inhibition term is due, in part, to the fact that many conventional cell reaction processes never reach cell concentrations where the cell inhibition term becomes important. For instance, in batch fermentation processes cell concentrations never reach high values because initial substrate concentrations are kept low to prevent substrate inhibition. In conventional continuous fermentation and mammalian cell cultivation processes a portion of the cell suspensions may be lost due to the removal of reaction products. Recent efforts have been made to improve cell mediated reaction productivities by increasing cell concentrations in biological reactors. The following is a brief discussion of the current literature with regard to increased cell concentrations in: (1) fermentations systems; and (2) mammalian culture systems.

Fermentation Systems

In an attempt to increase reaction productivities, process systems for yeast fermentation have been designed to permit cell concentrations to remain high while reducing the effect of product inhibition. For instance, Minier and Coma use a pulsed pack column to maintain high cell concentrations and reduce product inhibition by immediately removing product with an extraction solvent, 1-dodecanol. Column pulsation increases the interfacial area between dodecanol and the aqueous fermentation broth. Murphy uses a similar extraction process. Although these coupled processes are successful in increasing productivities, their shortcomings are that the extraction solvent often has an inhibitory effect on cell growth and cell production, and solid supports or cell recycle are still necessary to maintain high cell concentrations.

Cysewski and Wilke reduced product inhibition through vacuum fermentation and increased productivities by using recycle to maintain high cell concentrations. Maximum productivity for their process was found at yeast cell concentrations in the 60–100 g/l range. By comparison, conventional batch and continuous processes maintain maximum productivities at about 5 g/l. Since overall productivity is a function of the amount of yeast present, those systems which can maintain higher cell concentrations will have greater yields. However, it is at the increased concentrations that cell inhibition begins to affect the growth rate and the formation of product. These inhibitory effects need to be more accurately modeled. Processes which use recycle are not ideally suited for kinetic studies because as cells are removed they may go into a stationary phase of growth which may take some time to reverse upon reentrance to the fermentor. The proposed CCBR circumvents the need for cell recycle and will work well in the investigation of growth kinetics for densely packed cultures.

In conventional systems, prevention of cell-wash out in fermentation processes has been accomplished with retaining filters, immobilization of cells on solid supports, cell recycle, or a combination of recycle with membrane separation, centrifugal separation or settling techniques. Shortcomings exist for all of these methods. Membranes and filters can easily become clogged, especially when high cell concentrations are used. Membrane integrity is also a problem. The replacement cost of clogged or damaged membranes and the shutdown for cleaning of clogged filters can be prohibitive. Drawbacks for recycle processes have already been mentioned. Immobilization of cells on solid supports has two main disadvantages. First, the immobilization procedure may alter physiological functions of the cells. Secondly, the mass transfer to and from cells held within a permeable support structure is limited. The CCBR will eliminate the clogging and mass transfer problems associated with other processes.

Mammalian Cell Growth in Culture

Growth conditions for mammalian cells are receiving increased attention because of the need to improve production of human and animal health related products such as monoclonal antibodies. Product inhibition effects are less significant because product concentrations are usually very low. Cell inhibition effects, on the other hand, are usually an important consideration for mammalian cell cultures.

Product concentrations in cell mediated reaction processes are often on the order of milligrams per liter of tissue culture for batch tissue culture operations. Limiting factors in cell productivity have been the ability to simultaneously maintain high cell concentrations and provide a mechanism for gentle agitation to create good mass transfer to the shear sensitive hybridoma cells. One successful method for maintaining high cell concentrations has been to use hollow fibers surrounded by a polymeric sponge matrix. Cells proliferate in the sponge matrix, reaching concentrations nearing those in mammalian tissue. The reaction substrate flowing through the hollow fibers is metabolized by the cells to form the product of interest with productivities of three orders of magnitude greater than conventional batch processes. However, mass transfer limitations are a major limitation for accurate determination of cell growth kinetics in the hollow fiber processes. Another device developed by Fazekas de St. Groth, produces cells and their products at a constant high rate. The device uses a floating mechanism for agitation which provides adequate mass transfer. However, if substrate flow rates are too large, cells will be lost from the device in a similar way as they would in any continuous stirred vessel.

The current invention will provide adequate flow rates, a gentle mixing environment and will retain high cell concentrations. Thus the invention will not only be a useful technique to elucidate mammalian cell growth kinetics, but may also lead to the development of a more efficient high productivity cell culture system.

Production rates of monoclonal antibodies have in particular been very limited because of the cloning process and the need to isolate relatively small amounts of antibody from relatively small cell cultures. Practical difficulties in properly feeding such cultures and in easily and selectively removing the antibody contained in the culture media have further limited the volume of antibody which can economically be produced. This in turn has prevented uses of such antibodies because of the attendant high costs of such substances.

Many attempts have been made to enhance productivity in bioreactors by increasing the cell concentrations in the reactors to allow more manufacturing capability without increasing volumes. There are also reports that in some instances, such as in the production of monoclonal antibodies, that enhanced yields on a per cell basis are achieved at high density, perhaps because of redirection of metabolic energies reproductive activities to metabolic synthesis of antibody. Presently, even the best suspension culture systems only approach 5-10% of the cell density found in living organs. Somewhat higher densities have been achieved in systems where cells are trapped in hydrogel beads or hollow fiber systems. In each instance, however, reactor design limits maximum productivity. In summary, better reactors are needed which provide a low-shear well-mixed environment to maintain dense suspensions without cell washout. Such systems will also be ideally suited for studying reaction rates and media utilization in dense cultures. Following will be a discussion of the various strategies used for enhancing productivity in cell cultivation processes. The emphasis will be on techniques used in monoclonal antibody production from mouse spleen cells hybridized with culture adapted myeloma cells. However many of these procedures are applicable to cell culture in general.

In most tissue culture research laboratories common methods of small scale hybridoma cultivation use disposable plastic culture vessels with volumes ranging from 200 ul to 300 ml. Batch culturing in an incubator typically results in cell suspensions of $10^4$ to $10^5$ cells per ml and antibody concentration levels between 10 and 74 micrograms per ml depending on the hybridoma cell line and culture conditions. Periodic flushing of cells from the bottom of the culture vessel results in an increased growth rate as mass transfer limitations are reduced. Although useful for obtaining an ample supply of antibodies for research, such techniques are obviously not suitable for production purposes, nor are they ideal for obtaining all the kinetic parameters useful for describing growth, inhibition, and MoAb yield. Highly efficient bioreactors are urgently needed for laboratory use.

To increase antibody yields, many laboratories have used the mouse ascites method of cell culturing. Hybridoma cells are injected into the peritoneal cavity of mice and then harvested after six to twenty days. Because of near ideal culture conditions, cell densities greater than 10 cells per ml have been attained in our laboratory with antibody levels as high as 20 mg/ml. Others have reported levels of 5 mg/ml. Unfortunately, large scale antibody production requires maintaining substantial numbers of mice, and production yields are highly variable in ascites. Also, mouse immunoglobulins and other proteins appear in the ascitic fluid, creating separation problems.

Because of evidence that higher cell densities will result in increased reactor productivity, laboratory scale vessels that reduce culture medium diffusion problems through slow agitation have become popular. Roller bottles and spinner flasks have both been used for batch cell culture in the laboratory. Roller bottles are placed horizontally in an incubator and slowly rolled with the use of a motor driven stand. The continuous mixing results in increased cell densities and antibody yields through reduction of mass transfer limitations. Similarly, the spinner flask has been used with a suspended magnetic stir bar to obtain continuous mixing. Both of these vessels have the advantage of being suitable for hybridomas and anchorage dependent cell cultures. Cell densities between $10^5$ to $10^6$ cells per ml, with antibody yields of 50 to 140 micrograms per ml, have been achieved in our own laboratory and also reported by others. Although the agitated batch vessels maintain both cell and antibody concentrations higher than traditional batch culture plates and flasks, antibody yields are still well below those obtained from dense cell suspensions in ascites. Therefore, they are not well suited for identifying kinetic constants which describe dense systems. Also, these processes are not ideal for studying substrate utilization because of the accumulation of metabolic by-products. For this latter information, some form of flow through bioreactor is needed to permit growth and production measurements.

Continuous systems can provide useful information on substrate utilization and productivity in denser suspensions, and also information for verifying kinetic parameters. They are also useful commercially because they eliminate the reactor down time normally associated with batch processes. This is especially important in cultivating mammalian cells with slow growth rates. The biotechnology industry is stressing the need for continuous MoAb production. Companies like Hybritech (Los Angeles, CA), Invitron Corporation (St. Louis, MO; a spin-off of Monsanto Co.) and other leaders in biotechnology have developed large 100 liter vessels for mammalian cell cultivation on a continuous basis. The continuous stirred tank reactor (CSTR) is the most common of continuous reactor vessels. For biological systems, the terms "chemostat", "cytostat", "mixed flow reactor", and "perfusion reactor" have all been used to describe the continuous stirred vessel. Variations include "fed batch" and "semi-continuous fed batch" reactors. Typically, cell densities near $10^5$ to $10^6$ cells per ml and antibody levels of two to 300 migrograms per ml[2,5] have been achieved in the mixed flow reactor.

To further increase tissue density, and hence reactor productivity in CSTRs, several approaches have been taken. One technique has been immobilizing on microcarriers to prevent washout of the cell culture. Microcarriers, however, are limited to anchorage dependent cells. Encapsulation of cells within a calcium alginate gel and hydrogel have also been used to prevent washout but this technique introduces mass transfer limitations. Stephanopoulos has obtained yeast densities of up to $3 \times 10^7$ by using an inclined exit port in a CSTR. The technique takes advantage of an enhanced settling phenomena first observed by Boycott and more recently analyzed by Herbolzheimer and Acrivos. Feder and Tolbert have also demonstrated the technique for mammalian cells attached to microcarriers. Densities in these systems are still limited, however, when working with small unicellular suspensions with slow growth rates. Recycle techniques have also been devised which used settling tanks, centrifuges or membrane filters to recover cells or microbes and return them to the reactor. Disadvantages with these include changes in physiology of recirculated cells, accumulation of toxins, inhibitors and contaminants, clogging or breakage of expensive and delicate membranes used to separate cells from products, and inefficiencies in settling tank separation schemes.

Recently, a new bioreactor has gained much attention, the hollow fiber reactor. This system uses polymer fibers with sub-micron size pores that are placed in a shell and tube arrangement. Mammalian cells are injected into the shell space of the reactor with various modes of operation for supplying medium. The closed shell configuration, which has been used most frequently, feeds medium through the fiber lumen. Fresh medium diffuses through the fiber matrix into the shell space and spent medium passes back into the bulk stream. It has been suggested that the cross flow configuration, in which medium is supplied directly to the cells through a shell side port and exits through the fiber lumen, more evenly distributes the flux of nutrients throughout the reactor. Variations of the crossflow mode have included delivery of air and carbon dioxide through the fiber lumen, thus creating a better interface for both oxygen transport and pH control.

The hollow fiber reactor has several advantages over the traditional CSTR or cytostat. Cultures can be grown in a low shear environment at high cell and antibody concentrations. This reactor also adapts to anchorage dependent cells where the large surface areas of the fibers can support very large numbers. The greatest advantage this reactor has over other systems is the ability of the hollow fiber membranes to act as an ultrafiltration unit and to concentrate the large molecular weight products in the shell space. Hybridoma cell densities of $10^7$ to $10^8$ cells per ml have been reported, with MoAb levels ranging from 400 to over 6000 micrograms per ml.

Unfortunately, the hollow fiber bioreactor has limitations. As cell concentrations approach $10^8$ cells per ml or more, the interstitial area of the fibers fill with cells. High mass transfer resistances readily occur in a system where molecular diffusion is the only form of transport of medium. Fouling of the membrane is also possible because of protein adsorption. In the cross flow configuration, limitations are still prevalent since the pressure gradient necessary for transport of nutrients and waste products from shell to tube side can increase the likelihood of fiber fouling. These mass transfer problems can lead to regions of low viability and productivity.

Fluidized bed reactors have been used for many years in the area of microbial fermentation. The excellent mixing characteristics or fluid dynamics of this type of reactor have made it a successful tool for biological systems. A variation of the fluidized bed reactor, the airlift fermentor, has been used by Celltech Limited (Berkshire, U.K.). These 10–1000 l vessels can accommodate cell levels of $3 \times 10^6$ per ml with antibody levels of up to 260 micrograms/ml. The major disadvantages with airlift systems result from the presence of the gas-liquid interface; this can cause protein foaming, cell death, and denaturing of products and nutrients. Also, like most fluidized reactors, they are difficult to operate continuously without resulting in cell washout. Light particles such as mammalian cells are difficult to maintain at even moderate densities, with only gravitational forces preventing elution. As in CSTRs, microcarriers, gels (Bellco Biotechnology, Vineland, NJ, has recently marketed a Hydrogel bioreactor), or outlet membranes can be used to alleviate washout in fluid beds, but the limitations of these techniques still persist. Another way to circumvent washout is to use a fixed bed system. One example is ceramic supports such as those used by Marcipar, et al. In some ways, this approach is like the hollow fiber reactor, but without the benefit of product purification.

The need for a dense suspension of cells to achieve optimal production of antibodies (and other products) is evident from comparing yields achieved with the currently used bioreactors and culture techniques. Cell densities above $10^7$ cells per ml have resulted in the highest yields of MoAb. Higher concentrations of antibodies reduce the cost and difficulty associated with purification. Besides cell density, efficient mass transfer is a major concern. Ascites production uses the circulation system of animals to produce milligram quantities of MoAb. Production levels in culture dishes and flasks is two to three orders of magnitude lower due in part to diffusion limitations. With steady mixing these limitations and problems are reduced but not eliminated. Continuous reactors increase yields and maintain the necessary mixing, but are not capable of achieving cell densities or productivities comparable to ascites or hollow fiber reactors.

Accordingly, there remains a need for an apparatus and method for continuously culturing, feeding and extracting cell products from microbial cultures while allowing maintenance of the cultures. There also remains a need for continuous bioreactors which allow study of various process parameters on a defined cell population to provide more accurate data of affects caused by various control parameters.

BRIEF DESCRIPTION OF THE DRAWINGS

The preferred embodiment of the invention is illustrated in the accompanying drawings, in which:

FIG. 4 is a graph showing the interface position versus flow rate for suspensions of dead yeast cells in a reactor according to this invention;

FIG. 5 is a graph showing a size distribution of dead yeast cells contained in effluent from a bioreactor of this invention;

FIG. 8 is a graph showing a comparison of results from a model and experimental results for ethanol productivity with time; and FIG. 9 is steady-state fermentation run. Region I is the unsteady-state region. Due to an upset the system did not come to its first steady-state until 75 hours as shown in Region II. This was at a dilution rate of 0.2 hu$-1$. The Region II steady-state concentrations were 34 g/l and 23 g/l for ethanol and glucose, respectively. Due to a drop in dilution rate to 0.15 hr$^{-1}$ at about 100 hr the system came to second steady-state as shown in Region III. This higher steady-state yielded a glucose concentration of 10 g/l and an ethanol concentration of 47 g/l or conversion of 90% and an ethanol yield of 0.5 g ethanol/g glucose consumed.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

Figure 1:
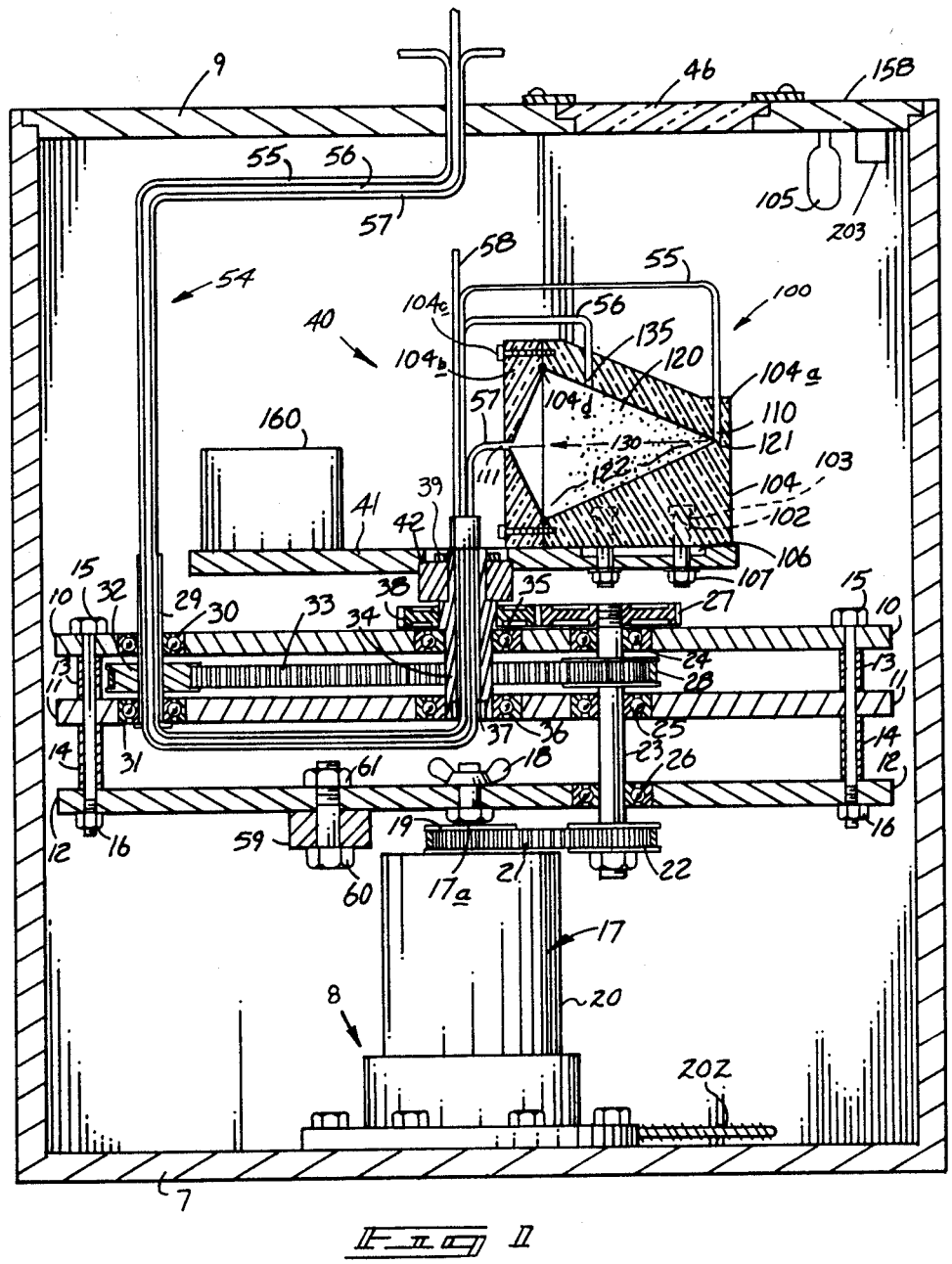
FIG. 1 is a side sectional view of a bioprocessing apparatus according to this invention.

FIG. 1 shows a preferred embodiment of flow-through centrifugal bioreactor 9 to the present invention. Bioreactor 9 includes a case 7, stationary base 8 and a rotor frame composed of three spaced-apart, horizontal, circular plates 10–12. Each of the plates 10–12 is provided with a plurality of apertures which extend through the plate near its periphery. Corresponding apertures in each of the plates 10–12 are axially aligned with one another. A plurality of tubular spacers 13 are positioned between the plates 10 and 11 and a further plurality of tubular spacers 14 are positioned between the plates 11 and 12 in alignment with the aforementioned apertures, only two of the tubular spacers 13 and two of the tubular spacers 14 being visible in FIG. 1. Bolts 15 extend through the respective axially aligned apertures in the plates 10–12 and the corresponding tubular spacers 13 and 14, each bolt 15 being held in place by a corresponding respective nut 16. The rigidly connected plates 10–12 are driven by a motor 17 with motor shaft 17a which is fixed to the center of the lower plate 12 by conventional means, shown as a wing nut 18. A stationary toothed pulley 19 is mounted on the motor housing 20, the stationary pulley 19 being connected, via a toothed belt 21 to a toothed pulley 22 which is fixed to the lower end of a countershaft 23. The countershaft 23 extends through apertures in the plates 10–12 within which respective ball bearings 24–26 have been fixedly positioned. A gear 27 is nonrotatably connected to the upper end of the countershaft 23 and a toothed pulley 28 is mounted to the countershaft 23 between the plates 10 and 11 in a fixed position.

As shown to the left in FIG. 1, a rigid, hollow shaft 29 is positioned within further apertures provided in the respective plates 10 and 11 and operatively positioned so as to be rotatable in respective ball bearings 30 and 31 which are respectively fixed in these additional apertures in the respective plates 10 and 11. A toothed pulley 32 is fixedly connected to the hollow shaft 29 and coupled to the pulley 28 via a toothed belt 33.

A hollow shaft 34 extends through centrally positioned apertures in the plates 10 and 11, this hollow shaft 34 being positioned for rotation within ball bearings 35 and 36 which are carried respectively in the central apertures of the respective plates 10 and 11, a spherical bearing 37 being provided for supporting the lower end of the hollow shaft 34. A gear 38 is fixed to the hollow shaft 34 and meshed with the gear 27, the gears 38 and 27 having a 1:1 ratio. The upper end of the hollow shaft 34 is threaded to receive a ring nut 39.

A centrifuge turntable assembly 40 according to the invention is connected to the upper end of shaft 34. The turntable assembly includes a turntable member 41, preferably constructed of aluminum. The turntable member 41 has a central aperture through which the hollow shaft 34 extends, and is clamped between the ring nut 39 and a flange 42 which extends radially outward from the hollow shaft 34 above the gear 38.

The turntable member is adapted to mount a reactor 100 and a counterbalancing weight 160 thereto. Reactor 100 is preferably mounted in an adjustable manner such as by using a plurality of bolts 102 which extend through apertures 103 in reactor 104. The bolts 102 also extend through slotted apertures 106 in the turntable. Nuts 107 or other suitable means allow tightening of the bolts 102 and reactor block 104 to turntable 41. The reactor can be positioned at different radial positions to adjust balance and centrifugal force range.

The reactor 104 is preferably made in two pieces with a main body 104a and a cap 104b. Cap 104b is mounted to main body 104a using a suitable connection means such as bolts 104c. A seal such as o-ring seal 104d is preferably used between the main body and cap. The reactor is preferably made of a clear material to allow observation using a stroboscopic light 105 or other suitable means during rotation. An observation port 46 is included in the base housing.

The reactor 104 is also provided with an inlet 110 and outlet 111. Inlet 110 is positioned radially outward of the outlet thus orienting the reactor so that a flow of media within the reactor chamber 120 from inlet toward the outlet is counter to the microbes which settle outwardly due to the centrifugal force caused by rotation of the turntable assembly 40. The counterflow of the medium provides an inwardly directed centripetal force to the centrifugally accelerated microbes.

The reactor chamber preferably includes an inlet passage 121 with relatively small cross-sectional flow area thus providing a relatively high flow rate velocity to counteract the centrifugal migration of the microbes. The reactor also includes a reaction zone 122 which extends from the inlet in an inward direction which is preferably along a direct radial line. The reaction zone is preferably conical with an axis of revolution defining the interior reactor surfaces about a longitudinal chamber axis 130. The inlet passage is preferably cylindrical about axis 130. The reaction zone is preferably a monotomically diverging cone in general configuration thus providing a continuously decreasing flow velocity through the reaction zone for a given flow volume into and from the reactor. This velocity gradient allows a variety of cells or microbes contained in a culture to find their own point of equilibrium. The fluidization depends on medium flow rate, particle mass, size and surface phenomenon with the fluid.

Reactor 104 preferably also includes one or more reaction zone taps 135 which can be used to remove excess microbes which may develop during extended culturing periods. The extracted cells and medium can also be processed for endogenous cell products removed as a desired product, or used in other cultures.

Figure 2:
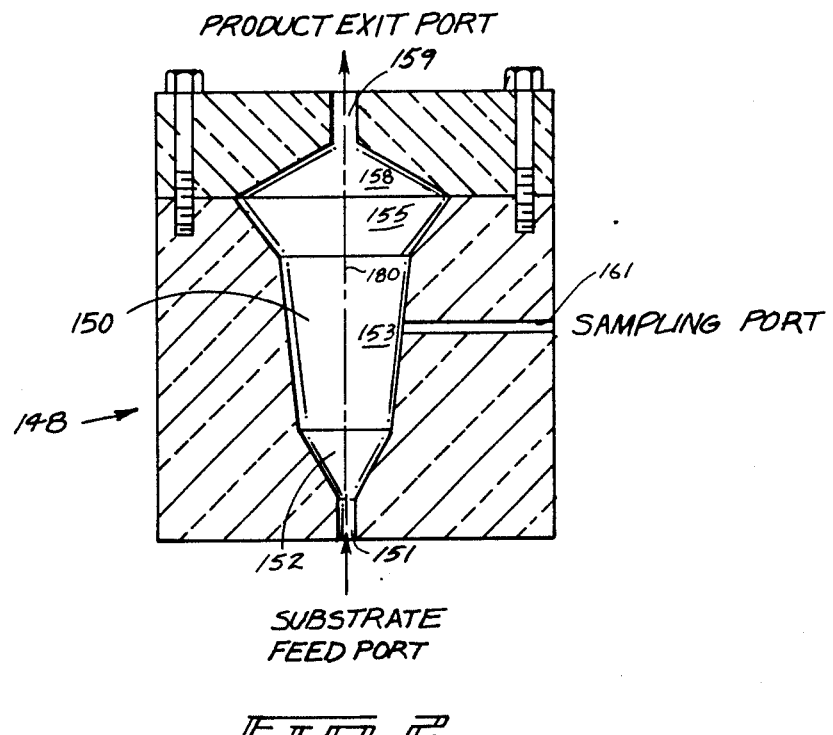
FIG. 2 is an enlarged cross-sectional view of an alternative embodiment reactor which can be used in the bioprocessing apparatus of FIG. 1.

FIG. 2 shows an alternative reactor 148 having a chamber design 150 which includes an inlet passage 151 and a first zone 152 which is adjacent thereto. The first zone is conically diverging in cross-sectional flow area from the inlet passage toward the rotational axis. A second zone 153 is adjacent to the first zone and is adapted to maintain the bulk of the culture therein. The second zone has a second divergence indicative of the increase in cross-sectional flow area as a function of the position along the longitudinal axis of the chamber. The reactor further includes a third zone 155 which is also diverging along the flow path. The first, second, and third divergence values associated with first, second and third zones 152, 153, and 155 are related by the first divergence being greater than the second, and the third divergence being greater than both. The reactor chamber 150 further has a fourth zone 158 which converges along the flow path to the outlet passage 159. A reaction zone side tap 161 is provided in the sidewall of second zone 153.

FIG. 1 shows a bundle 54 consisting of four flexible tubes 55, 56, 57, and 58 is fixed within an opening which is coaxial with the drive shaft 17 and may be formed, for example, in a cover 158 associated with the housing of the centrifuge. The bundle 54 of tubes 55–58 extends radially outward from the axis of rotation of the drive shaft 17 to the hollow shaft 29, downwardly through the hollow shaft 29, radially inwardly to beneath the hollow shaft 34 and upwardly through the hollow shaft 34 so that each of the tubes 55–57 is positioned above the reactor 104 for viewing the transparent lid through window 46. The flexible tube 55 is connected to the inlet of the reactor. The flexible tube 56 is connected to the side tap of the reactor, and the flexible tube 57 is connected to the outlet of the reactor. Tube 58 is a dead-ended tube supplied with a $CO_2$-air mixture which permeates into the other tubes for pH adjustment.

A counterweight 59 is provided beneath the plate 12, it being held in place by a bolt 60 and an associated nut 61. The counterweight 59 is positioned radially opposite to the pulley 22 and the countershaft 23 so as to balance the frame. The turntable is further provided with an adjustable counterweight 160 which is adjustably positioned on turntable 40 using bolts (not shown) or other suitable means similar to the connection of the reactor.

The bioreactor case 7 is advantageously provided with an electric resistance heating coil 202 and a temperature sensing thermocouple 203.

In operation, the drive shaft 17 of the drive motor drives the frame, including the horizontal plates 10–12, at a particular selected angular velocity w, for example at 1000 r.p.m. The toothed pulley 22, which is fixed to the countershaft 23, rotates about the axis of rotation of the drive shaft 17 and, because of its connection, via the toothed belt 21, to the toothed pulley 19 fixed to the housing of the drive motor, causes the countershaft 23 to rotate within the bearings 24–26. As a result of this movement of the countershaft 23, the gear 27 drives the gear 38 at an angular velocity of 2w because of the 1:1 gear ratio. As a result, the turntable 40, which like the gear 38 is fixedly connected to the hollow shaft 34, rotates at an angular velocity of 2w.

At the same time, the toothed pulley 28, rotating with the countershaft 23, drives the toothed belt 23 which, in turn, drives the toothed pulley 22 fixed to the hollow shaft 29. This causes the hollow shaft 29 to rotate about its own axis at an angular velocity of -w. As a consequence of this, the bundle 54 of the flexible tubes 55–57 does not become twisted and yet allows fluid communication into and out from the reactor 104 without the presence of any rotating seals. When properly balanced, the flowthrough bioreactor can be operated at speeds up to 2,000 r.p.m. for the purpose of maintaining a cell or microbe culture within the reactor while nutrient containing medium is counterflowed through the reactor against the centrifugal migration of the culture in a fluidized process.

The dynamics of the cultured cells can be modeled by considering a cell as a free body and subjecting it to a centrifugal settling force and balancing this with a countervailing centripetal flow resistance force. The settling velocity can be predicted using Stokes equation for low Reynolds numbers:

$$U_+ = \frac{w^2 r D^2 (P_1 - P_2)}{18 u} \quad (1)$$

where $U_+$ = particle terminal settling velocity
$D$ = particle diameter
$w^2 r$ = angular acceleration
$P_1$ = particle density
$P_2$ = fluid density
$u$ = viscosity of the suspending fluid The range of particle sizes and densities are then used to determine the range of flow velocities which are needed to maintain the cells within a desired reaction zone, such as zone 152 of FIG. 2. The more divergent zone 153 is used to settle all cells into zone 152 and prevent cell discharge through the outlet.

Figure 3:
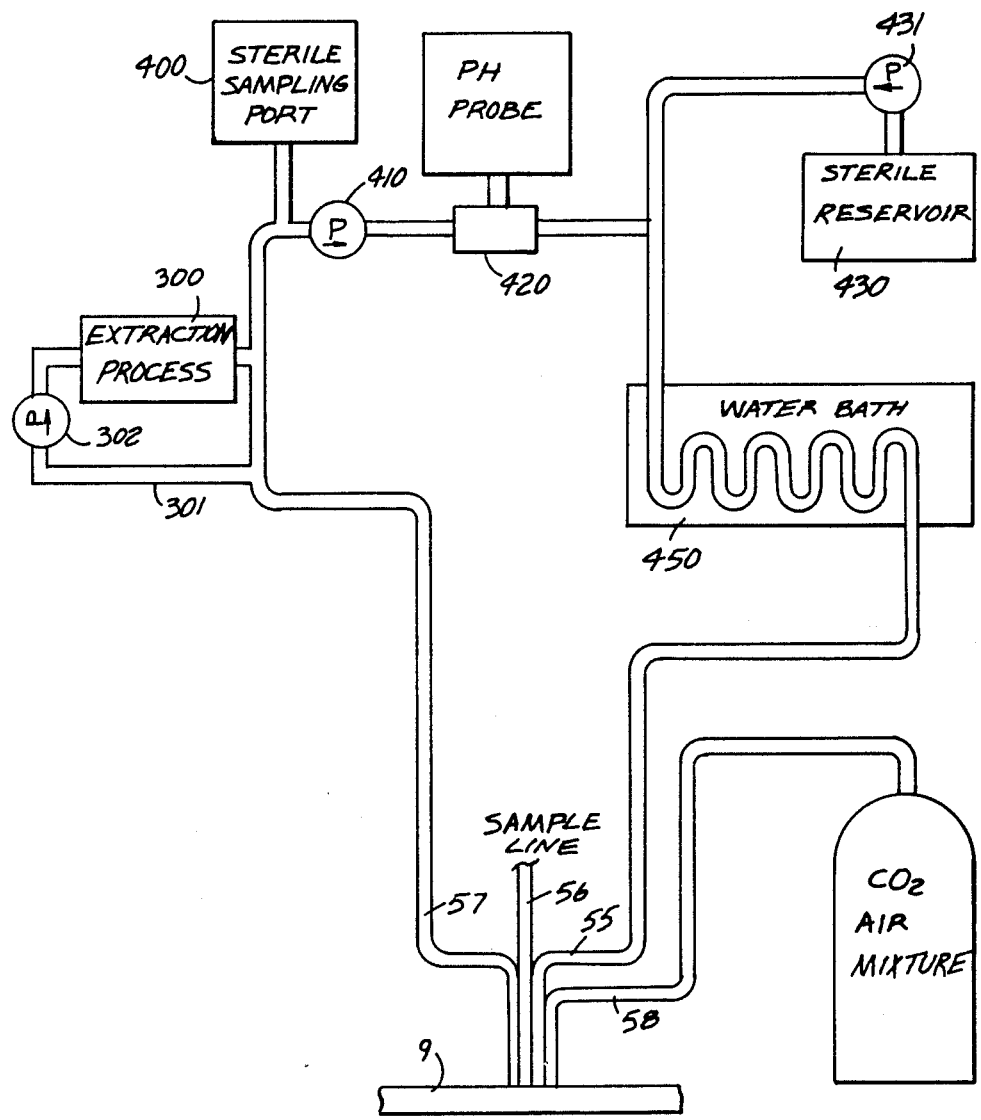
FIG. 3 is a process flow diagram showing the bioreactor of FIG. 1 connected in a recycle and extraction system to provide a preferred bioprocessing system according to the invention.

In some cases the modeling indicated above may be improved instead by using the following equation:

$$V_o = \frac{w^2 r D^2 (P_1 - P_2)}{150 u} \cdot \frac{e^3}{1 - e} \quad (2)$$

where $V_o$ = empty chamber average fluid velocity needed to fluidize
$e$ = void fraction associated with gas discharge from yeast or other cultures FIG. 3 shows a preferred system according to the invention. The system uses bioreactor 9 as described above. Outflow line 57 is connected to an extraction process 300 through a side loop 301 and circulated therethrough using pump 302. A suitable extraction process is an immunoaffinity column well known in the art.

The effluent is also connected to a suitable sterile sampling port 400. A pump 410 pumps the effluent through a pH probe 420. Makeup medium is injected from sterile reservoir 430 using pump 431. A water bath 450 advantageously conditions the flow for return to the reactor 104. A $CO_2$-air mixture is applied to tube 58 and is diffused through common walls of the tubes so that pH adjustment can occur.

The method and operation of this invention first involve obtaining a suitable continuous flow centrifugal bioreactor such as described above. The reactor is then charged with a microorganism or cell line to be produced. The turntable and reactor are then rotated to exert a centrifugal force on the individual cell particles.

A countervailing fluidizing flow of medium is commenced, preferably with rotation of the reactor to reduce risk of packing at the inlet passageway. The rotational speed and fluidizing flow rate are then adjusted to maintain the culture within a desired reaction zone. Medium is passed through the reactor from inlet to outlet to maintain fluidized suspension of the cells. Nutrients are introduced into the medium if not inherently provided by the medium. Additives which are useful for promoting cell growth, cell reproduction, cell production of desired byproducts or extraction of desired products can also be included in the medium. Medium can be either fresh or recirculated in a closed loop processing system. The medium is advantageously pumped using pump 410 which is accurate in displacement to provide the desired control of the reaction zone flow velocities so that positioning of the cultured cells is accurately maintained.

Example 1

Yeast

The organism used in this study was a non-flocculating strain of the yeast *Saccharomyces cerevisiae*, ATCC y-2034.

Medium

The medium used consisted of 100 g/L glucose, 8 g/L yeast extract, 1.3 g/L $NH_4Cl$, 0.11 g/L $MgSO_4$ $7H_2O$, 0.06 g/L $CaCl_2$, and 0.3 g/L silicone oil antifoam dissolved in tap water. The medium was autoclaved at 15 psig and 121° C. for 20–60 min depending on the volume.

Batch Fermentations

The innoculum was prepared in small batch fermentations. Erlenmeyer flasks containing 125 mL of medium were adjusted to pH 4.5 and then inoculated. The flasks were then incubated at 35° C. in a rotary shaker incubator. After approximately 24 h, the yeast was harvested and refrigerated at 4° C. until needed.

Fermentation Procedures

Before each fermentation, the bioreactor 9 and all connecting tubing were sterilized in an autoclave for 30 min at 15 psig and 121° C. To initiate fermentation 8–10 mL of concentrated yeast solution was fed into the reactor 104, while rotating at an angular velocity of 900 rpm, to avoid initial washout. After all of the yeast had entered the reactor the flow rate and angular velocity were slowed down to 0.5 mL/min and 400 rpm, respectively. Samples were then taken every 2 h to obtain unstead-state concentration profiles. The reactor was positioned to place the reaction zone at approximately 10 cm radius of rotation. Centrifugal acceleration of 30–50 g was used, typically 40 g. The recycle flow rate was held at 2 ml/min and the makeup flow rate of fresh medium was maintained at 0.1–0.2 ml/min.

Sampling and Analysis

During experiments, 2 mL samples were taken periodically from the effluent stream to measure the cell viability as well as ethanol, glucose, and cell concentrations. Ethanol concentrations were determined enzymatically using a SIGMA No. 332-UV assay kit. Cell concentrations were determined on a dry weight basis by recording the absorbance of light at 610 nm of a diluted sample. The actual concentration was then calculated using a linear calibration graph of absorbance versus dry cell weight concentration. Glucose concentrations were determined enzymatically using a SIGMA No. 15-UV assay kit. The yeast cell viability test was done by using a selective staining technique. In this procedure, a mixture of 1 part sample, 3 parts Wolford's stain, and 4 parts water was placed on a microscope slide. A manual cell count was then done under a microscope at 100X.

Studies were performed with dead and active yeast to assess the effect of a high gravity environment on suspension stability, cell viability, and the aggregation characteristics of the yeast. FIG. 4 shows the effect of dilution rate on interface position for dead yeast. Suspensions reached steady-state interface positions within 6 min. Bed expansion as a function of flow rate suggests that average porosities are increasing in a similar fashion as they would when superficial velocities are increased in conventional fluidized beds.

Live yeast, however, did not exhibit a strong correlation between interface position and superficial velocity. First, interface position remained relatively constant up to a certain dilution rate at which cells were bled out of the reactor. This dilution rate was in the range of 0.4–0.6 $h^{-1}$ depending on the centrifuge rpm. Secondly, it was more difficult to retain large quantities of live yeast within the reactor. For example, it was possible to operate the system filled with as much as 50 to 70% (wet volume) dead yeast while live yeast could only be retained in the outermost 10–15% of the reactor. To a large extent, these differences can be attributed to entertainment of cells by $CO_2$ bubbles in active cultures. The use of antifoam allowed greater retention of live cells so that the outermost 25% of the reaction chamber was filled with yeast.

Figure 6:
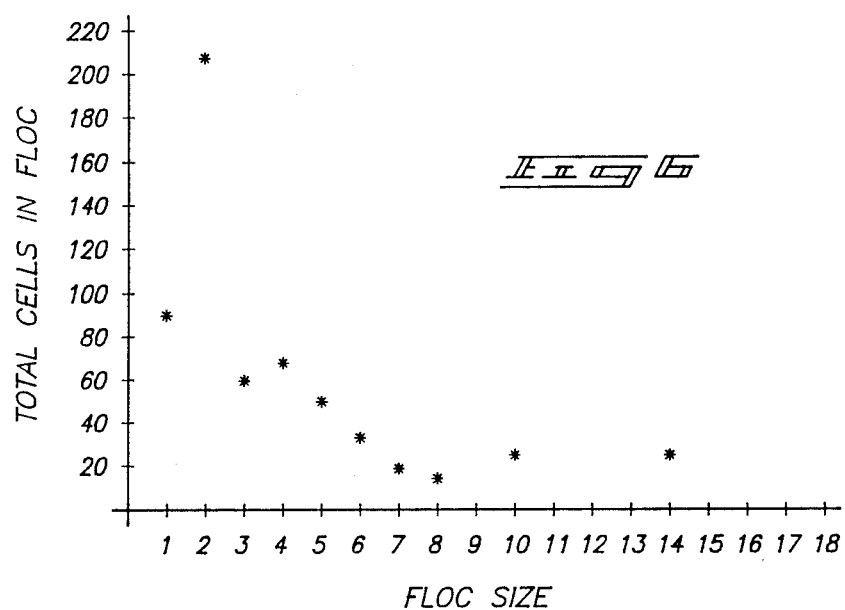
FIG. 6 is a graph showing a size distribution of live yeast cells contained in effluent from a bioreactor of this invention.

The increased aggregation of dead cells also played a role in making the dead cell beds more stable than those with live cells. Even though a non-flocculating strain of yeast was used, there was still some aggregation. FIGS. 5 and 6 show a distribution of cells from 250 flocs for dead and live cells, respectively. These plots reveal that there are a smaller number of single dead cells in suspension and a larger relative number of single live cells. The larger effective diameter of cell aggregates causes their settling velocity to increase. Thus, suspensions with larger, as well as greater numbers of flocs, in this case the dead cells, will have less of a problem with retention in the reaction chamber. In the studies with both dead and active yeast, there was very little difference in the floc distribution profiles before and after cells were exposed to the high gravity environment of the reaction chamber.

The viability of the innoculum fed to the reactor was normally in the 90–95% range. The viability of the yeast exiting the reactor could be kept in the range of 90–95% when dilution rates were maintained above 0.1 $h^{-1}$. Below this rate, viabilities would drop as low as 30% within 6 h but could be brought back to the 90–95% range within another 6 h by returning dilution rate to a value above 0.1 $h^{-1}$. These high viabilities compare well with those reported in ref. 2 which suggests that the large centrifugal forces in the reaction chamber do not have adverse effects on yeast cultures.

Cell buildup within the reactor also suggests that the system provides an adequate environment for growth. This was proven during runs where the cell concentration in the reactor was significantly reduced at high dilution rates. Following this, the yeast bed would rebuild itself after the dilution rate was decreased.

Figure 7:
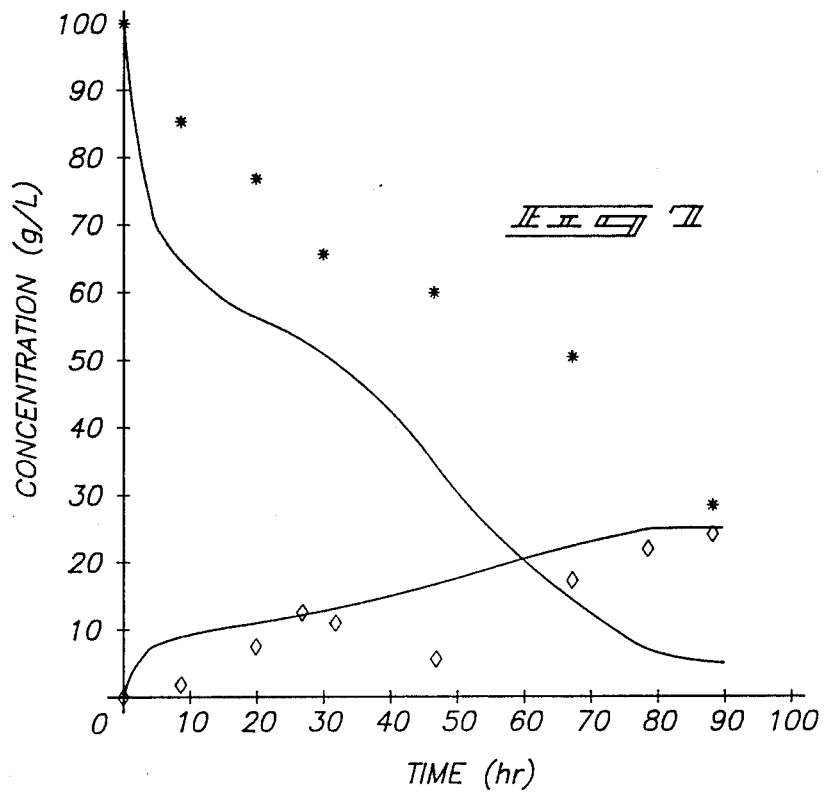
FIG. 7 is a graph showing a comparison of results from a model and experimental results for glucose and ethanol concentration time profiles. The solid lines are model predictions. The diamonds are ethanol production concentrations. The stars are glucose concentrations.

FIG. 7 shows the cell and substrate concentration versus time plot for unsteady-state operation during one run as compared to the model results for the operating conditions used during that run. FIG. 7 shows that the experimental product concentrations agree fairly well with the model, but the rate of substrate uptake is much lower than that predicted by the model. For this run the parameters of the model were found to be $$Y_{s/x} = 10.0$$
$$C_M = 1.0 \text{ g/L}$$
$$k_3 = 0.10 \text{ h}^{-1}$$

Productivities may also be obtained from the model given by eqs. (3)–(5). These results are shown in FIG. 8. This figure shows that the productivity of the reaction chamber is comparable to that of a CSTR, although the system has not yet reached steady-state. It should be noted here that the system requires a great deal of time to approach steady-state, and never really reached it, even after 90 h.

Example 2

Cultivation of Hybridomas in the Bioreactor of This Invention

The (CCBR) bioreactor 9 and system of FIG. 3 was adapted for mammalian cell work by adding an autoclavable sterile sampling system, on-line pH probe, a means for controlling pH (by simultaneous passage of media and an air-CO2 mixture through multi-lumen gas permeable silicone tubing), thermocouples and resistance coils (for temperature monitoring and control), and a sterile nutrient feed system. Two preliminary experiments (one eight day and one 17 day) have been performed using H21A1 mouse hybridomas to produce species cross-reactive IgM antibodies specific for major histocompatibility Class I antigens. Results from these studies show that cells remain viable, replicate normally, and that pH, medium throughput and bed porosity can be easily monitored and controlled.

To prepare the system for cultivation of hybridomas, the CCBR rotor is connected to the multi-lumen tubing. This rotor-tubing assembly and other tubing are then autoclaved. Once sterilized the rotor is attached to the anti-twister mechanism and connections to pump tubing made with a DuPont Sterile Connection Device SCD-IIB. Fresh culture medium containing 10% Hepes buffer in full DMEN (Dulbecco's Modified Eagle Medium consisting of 13% fetal bovine serum, antibiotics (penicillin and Streptomycin), $3 \times 10^{-5}$ M2-mercatoethanol) is fed to the CCBR. At this time a suspension of cells is added through feed tubing by means of a roller pump. Rotor rpm is maintained at 600 rpm (a g-force of approximately 40) and a pumping rate of 2 ml/min is used. For the 17 day trial run 300 ml of culture containing $1.25 \times 10^8$ total cells was fed to the system. This initial culture suspension contained 67% viable cells. Once in the reactor the cells form a dense suspension near the outermost diameter of the CCBR. Suspension densities range from 10 to 50% depending on medium flow rate through the reactor. Typical flows of 2 ml/min through the reactor are used resulting in a suspension density of about 30%. Once cells are in the CCBR fresh medium is added to the process at a rate of 0.1-0.2 ml/min. The fresh medium is run threough a 37° C. temperature bath to maintain optimum temperature for cultivation. Product is removed at 0.2 ml/min while medium is recycled from the product stream at a rate of 2 ml/min to maintain fluidization of the cell suspension. This recirculation also allows for conditioning of the medium by the cells. Feed of fresh medium alone was found to shock the culture leading to cell death after 3-5 days. Viabilities during the 17 day experiment ranged from 30-70% and varied as a function of fresh medium flow rate. Lower values of 0.12 ml/min led to the build-up of lactate causing a drop in pH to 6.8 or lower. This lead to an increase in cell death rate. Return of fresh medium flow to 0.2 ml/min was found to increase pH levels to between 6.9-7.2 and enhance viability. After 17 days of study the total cell number within the CCBR chamber was at $2.2 \times 10^8$ cells/ml with a viability of 57%. Product streams from the reactor typically contained cell concentrations of $2-4 \times 10^4$ cells/ml.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A method for long term culturing of cells or other microorganisms forming a microorganism culture, comprising:

installing a microorganism within a reaction chamber of a bioreactor having a rotatable rotor which mounts a reactor which defines at least portions of said reaction chamber; said bioreactor being capable of centrifugally rotating the reactor and reaction chamber;

rotating the microorganism culture contained within the reaction chamber to thereby create centrifugal forces acting upon the microorganisms forming the microorganism culture;

supplying a flow of fluid culture medium to the rotating rotor and reaction chamber;

controllably forcing fluid culture medium through the microorganism culture held within the reaction chamber in a manner which creates fluid dynamic forces on the microorganisms which are in opposition to the centrifugal forces applied to the microorganisms;

forming a velocity gradient within the fluid culture medium as the culture medium flows within the reaction chamber; said velocity gradient varying from a relatively faster velocity to slower velocities countervailing to the centrifugal forces acting on the microorganism;

fluidizing the microorganism culture by controlling the flow of fluid culture medium through the reaction chamber to maintain microorganisms of the microorganism culture in a fluidized mass within the reaction chamber;

suspending the microorganisms of the microorganism culture within the reaction chamber substantially balanced by countervailing fluid drag forces and centrifugal forces;

removing fluid culture medium from the rotating rotor and reaction chamber;

recirculating fluid culture medium removed from the rotating rotor and reaction chamber back through the reaction chamber;

feeding the microorganisms of the microorganism culture which are suspended in the reaction chamber by supplying suitable nutrients for the microorganisms in the fluid culture medium as the fluid culture medium is forced through the reaction chamber.

2. A method according to claim 1 wherein said suspending of the microorganisms of the microorganism culture within the reaction chamber is performed for at least one day.

3. A method according to claim 1 and further comprising extracting a desired product of the microorganism culture from the recirculating fluid culture medium while maintaining the microorganism culture suspended in the bioreactor.

4. A method according to claim 1 and further comprising extracting a desired product of the microorganism culture from the recirculating fluid culture medium while maintaining the microorganism culture suspended in the bioreactor; said extracting including removing said desired product from recirculating fluid culture medium using immunoaffinity binding.

5. A method according to claim 1 and further comprising treating recirculating fluid culture medium to adjust the pH of the recirculating fluid culture medium to maintain desired pH conditions for the microorganism culture.

6. A method according to claim 1 and further comprising:
sensing pH of recirculating fluid culture medium;
treating recirculating fluid culture medium to adjust the pH of the recirculating fluid culture medium to maintain desired pH conditions for the microorganism culture.

7. A method according to claim 6 wherein said treating is accomplished by passing carbon dioxide into the recirculating fluid culture medium.

8. A method according to claim 1 and further comprising:
sensing pH of recirculating fluid culture medium;
treating recirculating fluid culture medium to adjust the pH of the recirculating fluid culture medium to maintain desired pH conditions for the microorganism culture;
extracting a desired product of the microorganism culture from the recirculating fluid culture medium while maintaining the microorganism culture suspended in the bioreactor.

9. A method according to claim 1 and further comprising controlling temperature of recirculating fluid culture medium.

10. A method according to claim 1 and further comprising:
sensing pH of recirculating fluid culture medium;
treating recirculating fluid culture medium to adjust the pH of the recirculating fluid culture medium to maintain desired pH conditions for the microorganism culture;
controlling the temperature of recirculating fluid culture medium.

11. A method according to claim 1 and further comprising:
sensing the pH of recirculating fluid culture medium;
treating recirculating fluid culture medium to adjust the pH of the recirculating fluid culture medium to maintain desired pH conditions for the microorganism culture;
controlling the temperature of recirculating fluid culture medium;
extracting a desired product of the microorganism culture from the recirculating fluid culture medium while maintaining the microorganism culture suspended in the bioreactor.

12. A method for long term culturing of cells or other microorganisms forming at least one microorganism culture, comprising:
installing at least one microorganism within at least one reaction chamber of a bioreactor having at least one rotatable rotor which mounts at least one reactor which defines at least portions of said at least one reaction chamber; said bioreactor being capable of centrifugally rotating the at least one reactor and reaction chamber;
rotating the at least one microorganism culture contained within the at least one reaction chamber to thereby create centrifugal forces acting upon microorganisms forming the microorganism culture;
supplying at least one flow of at least one fluid culture medium to the rotating rotor and reaction chamber;
circulating at least one flow of at least one fluid culture medium to the rotating rotor, through the reaction chamber, and from the rotating rotor;
controllably forcing at least one fluid culture medium through the microorganism culture held within the at least one reaction chamber in opposition to the centrifugal forces applied to the microorganisms;
fluidizing the at least one microorganism culture by controlling the flow of the at least one fluid culture medium through the at least one reaction chamber to maintain microorganisms of the at least one microorganism culture in at least one fluidized mass within the at least one reaction chamber;
suspending the microorganisms of the at least one microorganism culture within the at least one reaction chamber substantially balanced by countervailing fluid drag forces and centrifugal forces; said microorganisms being suspended for periods of at least one day;
removing fluid culture medium from the rotating rotor and at least one reaction chamber;
feeding the microorganisms of the at least one microorganism culture suspended in the at least one reaction chamber by passing suitable nutrients for the microorganisms in the at least one fluid culture medium as the fluid culture medium is forced through the at least one reaction chamber.

13. A method according to claim 12 and further comprising extracting at least one desired product of at least one microorganism culture from recirculating fluid culture medium while maintaining the microorganism culture suspended in the bioreactor.

14. A method according to claim 12 and further comprising recirculating fluid culture medium removed from at least one reaction chamber back through the at least one reaction chamber.

15. A method according to claim 12 and further comprising:
recirculating fluid culture medium removed from the at least one reaction chamber back through the at least one reaction chamber;

extracting at least one desired product of at least one microorganism culture from recirculating fluid culture medium while maintaining the microorganism culture suspended in the bioreactor.

16. A method according to claim 12 and further comprising:
   recirculating fluid culture medium removed from the at least one reaction chamber back through the at least one reaction chamber;
   extracting at least one desired product of at least one microorganism culture from recirculating fluid culture medium while maintaining the microorganism culture suspended in the bioreactor; said extracting including removing said at least one desired product from recirculating fluid culture medium using immunoaffinity binding.

17. A method according to claim 12 and further comprising:
   recirculating at least one fluid culture medium removed from the rotating rotor and at least one reaction chamber back through at least one reaction chamber;
   sensing pH of recirculating fluid culture medium;
   treating recirculating fluid culture medium to adjust the pH of the recirculating fluid culture medium to maintain desired pH conditions for the microorganism culture.

18. A method according to claim 12 and further comprising:
   recirculating fluid culture medium removed from the at least one reaction chamber back through the at least one reaction chamber;
   sensing pH of recirculating fluid culture medium;
   treating recirculating fluid culture medium to adjust the pH of the recirculating fluid culture medium to maintain desired pH conditions for the microorganism culture;
   extracting at least one desired product of at least one microorganism culture from recirculating fluid culture medium while maintaining the microorganism culture suspended in the bioreactor.

19. A method according to claim 12 and futher comprising:
   recirculating fluid culture medium removed from the rotating rotor and at least one reaction chamber back through the at least one reaction chamber;
   sensing pH of recirculating fluid culture medium;
   treating recirculating fluid culture medium to adjust the pH of the recirculating fluid culture medium to maintain desired pH conditions for the microorganism culture;
   extracting at least one desired product of at least one microorganism culture from recirculating fluid culture medium while maintaining the microorganism culture suspended in the bioreactor; said extracting including removing said desired product from recirculating fluid culture medium using immunoaffinity binding.

20. A method according to claim 12 and further comprising:
   recirculating fluid culture medium removed from the rotating rotor and at least one reaction chamber back through the at least one reaction chamber;
   sensing pH of recirculating fluid culture medium;
   treating recirculating fluid culture medium to adjust the pH of the recirculating fluid culture medium to maintain desired pH conditions for the microorganism culture;
   extracting at least one desired product of the microorganism culture from recirculating fluid culture medium while maintaining the microorganism culture suspended in the bioreactor;
   controlling temperature of recirculating fluid culture medium.

21. A method according to claim 12 and further comprising extracting at least one desired product of said at least one microorganism culture from fluid culture medium removed from the rotating rotor at least one reaction chamber.

22. A method for long term culturing of cells or other microorganisms forming at least one microorganism culture, comprising:
   installing at least one microorganism within at least one reaction chamber of a bioreactor having at least one rotatable rotor which mounts at least one reactor which defines at least portions of said at least one reaction chamber; said bioreactor being capable of centrifugally rotating the at least one reactor and reaction chamber;
   rotating the at least one microorganism culture contained within the at least one reaction chamber to thereby create centrifugal forces acting upon the microorganisms forming the microorganism culture;
   supplying at least one flow of at least one fluid culture medium to the rotating rotor and reaction chamber;
   controllably forcing at least one fluid culture medium through the microorganism culture held within the at least one reaction chamber in opposition to the centrifugal forces applied to the microorganisms;
   forming a velocity gradient within the fluid culture medium as the culture medium flows within the reaction chamber; said velocity gradient varying from a relatively faster velocity to slower velocities countervailing to the centrifugal forces acting on the microorganism;
   fluidizing the at least one microorganism culture by controlling the flow of the at least one fluid culture medium through the at least one reaction chamber to maintain microorganisms of the at least one microorganism culture in at least one fluidized mass within the at least one reaction chamber;
   suspending the microorganisms of the at least one microorganism culture within the at least one reaction chamber substantially balanced by countervailing fluid drag forces and centrifugal forces; said microorganisms being suspended for periods of at least one day;
   removing fluid culture medium from the rotating rotor and at least one reaction chamber;
   recirculating fluid culture medium removed from the at least one reaction chamber back through at least one reaction chamber;
   feeding the microorganisms of the at least one microorganism culture suspended in the at least one reaction chamber by passing suitable nutrients for the microorganisms in the at least one fluid culture medium as the fluid culture medium is forced through the at least one reaction chamber;
   sensing pH of recirculating fluid culture medium;
   treating recirculating fluid culture medium to adjust the pH of the recirculating fluid culture medium to maintain desired pH conditions for the microorganism culture;
   extracting at least one desired product of the microorganism culture from recirculating fluid culture medium while maintaining the microorganism culture suspended in the bioreactor; controlling temperature of recirculating fluid culture medium.

* * * * *